United States Patent
Shin et al.

(10) Patent No.: US 10,080,450 B2
(45) Date of Patent: Sep. 25, 2018

(54) FUNCTIONAL PILLOW

(71) Applicant: Joon Shik Shin, Seoul (KR)

(72) Inventors: Joon Shik Shin, Seoul (KR); Han Keel Yoo, Seoul (KR); Jin Ho Lee, Seoul (KR); Geun-Ho Roh, Gyeonggi-do (KR)

(73) Assignee: Joon Shik Shin, Seoul (KR)

( * ) Notice: Subject to any disclaimer, the term of this patent is extended or adjusted under 35 U.S.C. 154(b) by 218 days.

(21) Appl. No.: 14/951,249

(22) Filed: Nov. 24, 2015

(65) Prior Publication Data

US 2016/0073801 A1    Mar. 17, 2016

Related U.S. Application Data

(63) Continuation of application No. PCT/KR2015/005064, filed on May 20, 2015.

(30) Foreign Application Priority Data

May 23, 2014  (KR) .................... 10-2014-0062502

(51) Int. Cl.
*A47G 9/10* (2006.01)
*A61H 39/04* (2006.01)
(Continued)

(52) U.S. Cl.
CPC ........... *A47G 9/109* (2013.01); *A47G 9/1045* (2013.01); *A61H 23/0236* (2013.01);
(Continued)

(58) Field of Classification Search
CPC ...... A47G 9/10; A47G 9/1036; A47G 9/1063; A47G 9/1081; A47G 9/109;
(Continued)

(56) References Cited

U.S. PATENT DOCUMENTS 5,638,564 A * 6/1997 Greenawalt .............. A47G 9/10
 5/636
5,682,632 A * 11/1997 Cotroneo ................. A47G 9/10
 5/636

(Continued)

FOREIGN PATENT DOCUMENTS

| CN | 202173139 | 3/2012 |
| CN | 202820612 | 3/2013 |

(Continued)

*Primary Examiner* — Nicholas F Polito
(74) *Attorney, Agent, or Firm* — Sheridan Ross, P.C.

(57) ABSTRACT

Disclosed herein is a functional pillow. The functional pillow includes a back head placement part formed of a material with a predetermined shape and thickness and allowing the back of a user's head to be placed on an upper surface thereof when the user lies on the back; a pair of core parts coupled to the back head placement part, defining a space, into which an user's arm is allowed to be inserted, under both ends thereof, and configured to support a user's face on an upper surface thereof when the user lies on the side while the back of the user's head is placed on the back head placement part; a cervical vertebra support part coupled to the back head placement part, and protruding with an inclination from the back head placement part to support the cervical vertebra; and a pair of wing parts formed to be coupled to the pair of core parts and the cervical vertebra support part, formed to be upwardly bent with an inclination, and defining a space, into which user's shoulder is allowed to be inserted, thereunder.

17 Claims, 7 Drawing Sheets

(51) Int. Cl.
*A61H 23/02* (2006.01)
*A61M 21/00* (2006.01)
*A61M 21/02* (2006.01)

(52) U.S. Cl.
CPC ....... *A61H 39/04* (2013.01); *A47G 2200/143* (2013.01); *A61H 2201/0134* (2013.01); *A61H 2201/10* (2013.01); *A61H 2201/1604* (2013.01); *A61H 2201/1609* (2013.01); *A61H 2201/5048* (2013.01); *A61M 21/02* (2013.01); *A61M 2021/0022* (2013.01); *A61M 2021/0027* (2013.01)

(58) Field of Classification Search
CPC ...... A47G 2009/006; A47G 2009/1018; A47G 9/1045; A47G 2200/143; A61H 23/0236; A61H 39/04; A61H 2201/0134; A61H 2201/1609; A61H 2201/10; A61H 2201/1604; A61H 2201/5049; A61M 21/02; A61M 2021/002; A61M 2021/0027
USPC .......................................................... D6/601
See application file for complete search history.

(56) References Cited

U.S. PATENT DOCUMENTS

| | | | | |
|---|---|---|---|---|
| 5,727,267 | A * | 3/1998 | Keilhauer | A47G 9/109 5/632 |
| 6,704,958 | B2 * | 3/2004 | Gohl | A47G 9/1045 5/639 |
| 6,817,049 | B1 * | 11/2004 | Hall | A47G 9/10 5/632 |
| 6,823,546 | B1 * | 11/2004 | Hsu | A47G 9/007 5/636 |
| 6,981,288 | B1 * | 1/2006 | Hu | A47G 9/10 5/636 |
| 7,013,512 | B1 * | 3/2006 | Hsu | A47G 9/1081 5/636 |
| D645,693 | S * | 9/2011 | Rothbard | D6/601 |
| 8,161,588 | B1 * | 4/2012 | Anson | A47G 9/109 5/630 |
| D668,092 | S * | 10/2012 | Davis | D6/601 |
| D696,045 | S * | 12/2013 | Marinkovic | D6/601 |
| 8,893,334 | B1 * | 11/2014 | Wong | A47G 9/109 5/622 |
| 2004/0006822 | A1 * | 1/2004 | Milligan | A47G 9/10 5/636 |
| 2012/0017374 | A1 * | 1/2012 | Hunter | A47G 9/10 5/638 |
| 2013/0007961 | A1 * | 1/2013 | Noh | A61H 39/04 5/638 |
| 2013/0047339 | A1 * | 2/2013 | Kim | A47G 9/109 5/637 |

FOREIGN PATENT DOCUMENTS

| | | | | |
|---|---|---|---|---|
| CN | 203121824 | | 8/2013 | |
| JP | 1999-018895 | A | 1/1999 | |
| JP | 2000-139656 | A | 5/2000 | |
| KR | 10-0718661 | B1 | 5/2007 | |
| KR | 10-2009-0031201 | A | 3/2009 | |
| KR | 10-2012-0005893 | A | 1/2012 | |
| KR | 20-0472755 | Y1 | 5/2014 | |
| KR | 101418696 | B1 * | 7/2014 | ............ A47G 9/109 |
| WO | WO-9807358 | A1 * | 2/1998 | ........... A47G 9/1081 |
| WO | WO-2007114573 | A1 * | 10/2007 | ............ A47G 9/109 |
| WO | WO 2015084039 | A1 * | 6/2015 | ........... A47G 9/1081 |

* cited by examiner

FUNCTIONAL PILLOW

CROSS-REFERENCE TO RELATED APPLICATIONS

This application is a continuation application under 35 U.S.C. § 120 of International Application No. PCT/KR2015/005064 filed May 20, 2015, which claimed the benefit of Korean Patent Application No. KR 10-2014-0062502 filed May 23, 2014, the entire contents of each of which are incorporated herein by reference.

TECHNICAL FIELD

The present disclosure relates to a functional pillow, and more particularly, to a functional pillow capable of comfortably supporting the neck and the head of a person when the person sleeps on the back, and preventing the pressure of shoulder or the deflection of neck, and maintaining a balance, even when the person sleeps on the side.

BACKGROUND ART

In general, rest is as important as can be in functioning innumerable roles for human body, such as energy charge, vitality strengthening, growth, recovery, and immunity strengthening.

Most general rest in one's life is a sleep. There is no better rest than a good sleep. Accordingly, good sleep is important, and although the quality of sleep is affected by indoor temperature and humidity, a pillow leading to a good sleep is physically important.

When one misuses a pillow or sleeps in an abnormal posture, various diseases such as cervical vertebra facet joints disease of the neck, pain in the neck muscle, and ligament damage may be caused. In severe cases, a herniated cervical disc may even be caused. Most ideal sleeping posture is to allow the cervical vertebra to be straight (normal posture), so that muscles are allowed to have no tension.

It is desired to go to bed in a state in which the cervical vertebra is not overstressed such that when sleeping on the back, the neck is allowed to maintain a natural "C" letter curvature, and when sleeping on the side, the cervical vertebra and the thoracic vertebra are aligned in a straight line. Sleeping on one's stomach presses the nerves adjacent to the cervical vertebra and may thus cause numb arms or shoulder discomfort.

Function of a pillow is also important in that the pillow should support the neck while maintaining a normal alignment of the spine, and have a structure suitable for all the heads with various shapes.

When sleeping on the side, the pillow should have height greater than that when sleeping on the back, considering the height of the shoulder.

As a related art to functional pillows, Korean Patent Application Laid-open Publication No. 10-2012-0005893 discloses a functional pillow which is characterized by including: a back head placement part recessed in a shape corresponding to an outer shape of a back head; a cervical vertebra support part extending to a front side of the back head placement part, and formed in a curved surface corresponding to a curve of the cervical vertebra when the back head is placed on the back head placement part; and a flexible space formed such that one rear end of the back head placement part is recessed so as to adjust the size of the back head placement part according to the size of the placed back head of a user.

Also, Korean Patent No. 10-0718661 discloses a head rest for physical therapy characterized by including: a body formed in a cushion member having a predetermined shape and thickness; an upper cervical vertebra acupressure part formed in a curved shape at a predetermined height at one side of the body so as to support the upper cervical vertebra and including a head base acupressure cushion bar attached thereon in a curved shape so as to perform a deep acupressure to the head base portion; a back head acupressure part formed in a curved shape at a lower height than the upper cervical vertebra acupressure part at a position spaced a predetermined distance from the upper cervical vertebra acupressure part, and having a protrusion thereon; and a neck support part formed in a curved shape to incline from the upper cervical vertebra acupressure part.

However, these related arts have no function which maintains the balance of the cervical vertebra by comfortably supporting the neck and head when sleeping on the back and preventing the shoulder pressure or neck deflection when sleeping on the side. Thus, there is a limitation in that the diseases of the neck and shoulder caused by the pressure of the shoulder joint or the torsion of the cervical vertebra, which are frequently experienced by the people sleeping on the side, may not be prevented.

DISCLOSURE

Technical Problem

Embodiments of the present invention are directed to provide a functional pillow capable of comfortably supporting the neck and the head when a person sleeps on the back, preventing the pressure of the shoulder or the deflection of the neck, and maintaining a balance, even when the sleeps on the side, and providing an effect of acupressure and the retraction of the cervical vertebra to a user.

Technical Solution

According to an aspect of the present invention, there is provided a functional pillow including: a back head placement part formed of a material with a predetermined shape and thickness and allowing the back of a user's head to be placed on an upper surface thereof when the user lies on the back; a pair of core parts coupled to the back head placement part, defining a space, into which a user's arm is allowed to be inserted, under both ends thereof, and configured to support a user's face on an upper surface thereof when the user lies on the side while the back of the user's head is placed on the back head placement part; a cervical vertebra support part coupled to the back head placement part, and protruding with an inclination from the back head placement part to support the cervical vertebra; and a pair of wing parts formed to be coupled to the pair of core parts and the cervical vertebra support part, formed to be upwardly bent with an inclination, and defining a space, into which user's shoulder is allowed to be inserted, thereunder.

The back head placement part may further include an upper surface on which the back of the user's head is placed, and further include at least one first pressure distribution part on a surface thereof to distribute load pressure due to the back of the user's head.

The first pressure distribution part may include a ⊏-shaped line formed to penetrate in a ⊏-shaped form, at least one straight line, a line formed to penetrate with a shape of a polygon, a circle, an ellipse or a combination thereof, a groove formed in a shape of a polygon, a circle, an ellipse or a combination thereof.

The back head placement part and the pair of core parts may be coupled to each other to incline at a predetermined angle such that when a user lies on the back, the back of the user's head may be allowed to be placed on the back head placement part, and when the user lies on the side, the user's face may be supported by any one of the pair of core parts.

The ends of the pair of core parts may upwardly protrude to prevent the user's face from being deviated.

The core parts may further include at least one second pressure distribution part allowing load pressure due to a side of the user's head to be distributed.

The second pressure distribution part may be formed on at least one surface of upper and lower surfaces of the core parts.

The second pressure distribution part may include at least one pressure distribution groove formed on the upper surfaces of the core parts, and pressure distribution spaces defined on the lower surfaces of the core parts.

The pressure distribution spaces may be formed at portions adjacent to the cervical vertebra support part or the wing part The functional pillow may further include a sound source generator accommodated in the pressure distribution space.

The functional pillow may further include a first height adjustment pad allowed to be inserted into the lower space of the back head placement part.

The first height adjustment pad may include a hole portion capable of distributing load pressure due to the back of the user's head and increasing air permeability.

At lower ends of the pair of core parts, pad insertion parts into which second height adjustment pads allowing heights of the pair of core parts to be adjusted, may be formed.

The second height adjustment pads may be formed of materials with hardness greater than the pair of core parts.

The pair of core parts and the cervical vertebra support part may be formed in a multilayer structure formed of two or more materials with different hardness, and the hardness of a lower layer may be greater than that of an upper layer.

The cervical vertebra support part may include a cervical vertebra acupressure part formed to have hardness greater than those of the upper and lower layers of the cervical vertebra support part.

The cervical vertebra acupressure part may include a surface treated by a material having hardness greater than those of the upper and lower layers of the cervical vertebra support part, or include a portion formed such that a material having hardness greater than those of the upper and lower layers of the cervical vertebra support part is inserted into or attached to the portion.

Advantageous Effects

The cervical vertebra acupressure part may be formed to be attached/detached to a lower layer of the cervical vertebra support part.

A pair of mastoid zones distributing load pressure due to a user's neck and the back of the user's head may be formed at both lower ends of the cervical vertebra support part.

The pair of wing parts may be formed in shapes supporting user's jaw and neck by being inserted between user's neck and shoulder when the user lies on the side.

BEST MODE

Hereinafter, embodiments of the present invention may be described in detail with reference to the accompanying drawings.

First, it is to be noted that in giving reference numerals to elements of each drawing, like reference numerals refer to like elements even though like elements are shown in different drawings. Further, in describing the present invention, well-known functions or constructions will not be described in detail since they may unnecessarily obscure the understanding of the present invention.

Figure 1:
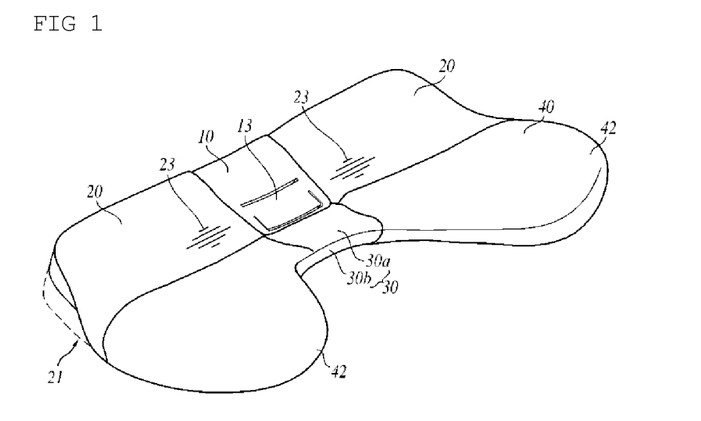
FIG. 1 is a perspective view illustrating a functional pillow according to an embodiment of the present invention.
Figure 2:
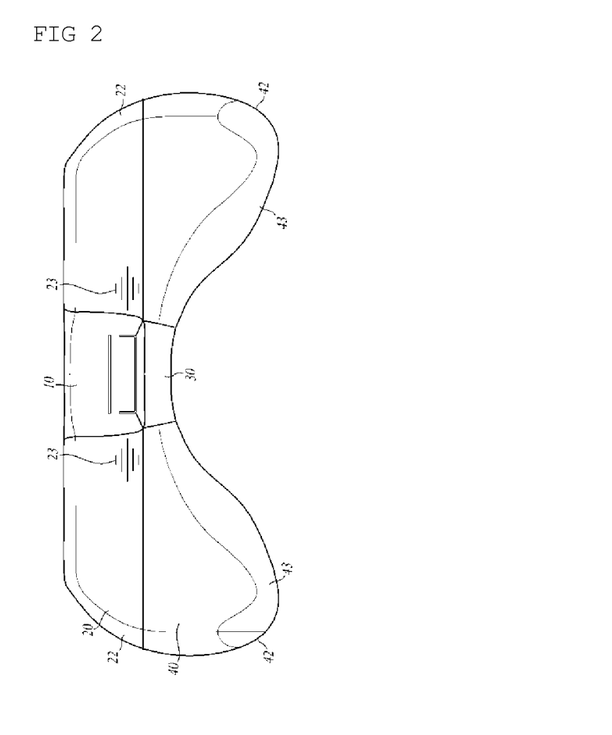
FIG. 2 is a plan view illustrating a functional pillow according to an embodiment of the present invention.
Figure 3A:
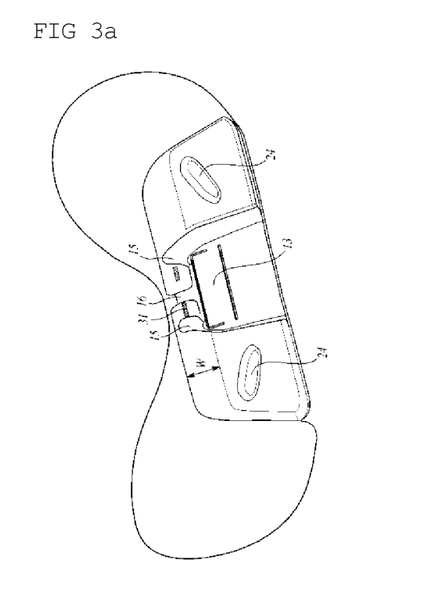
FIG. 3a is a rear view illustrating a functional pillow according to an embodiment of the present invention.
Figure 3B:
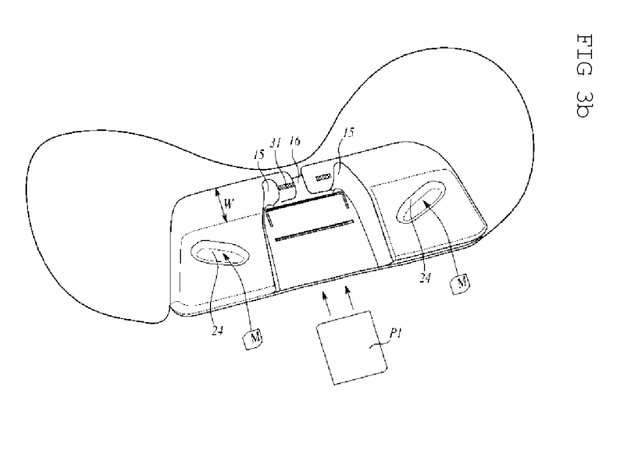
FIG. 3b is an exemplary view illustrating a process of inserting a first height adjustment pad and a sound source generator according to an embodiment of the present invention.
Figure 3C:
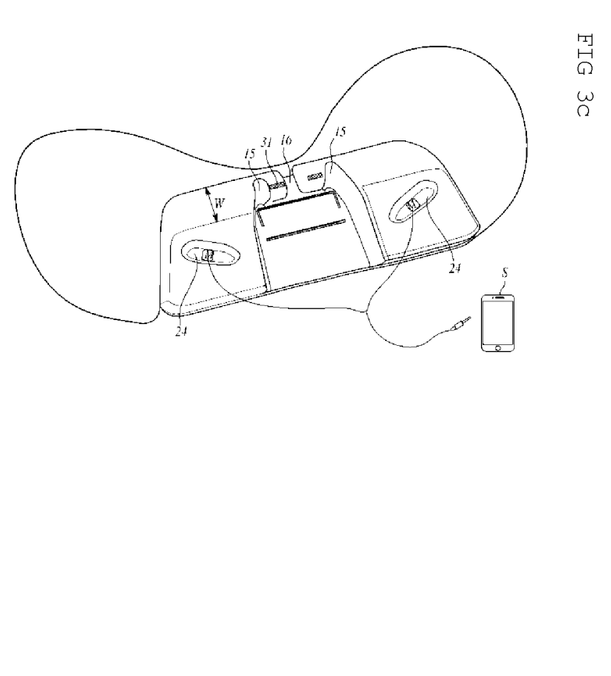
FIG. 3c is an exemplary view illustrating a case in which a sound source generator according to an embodiment of the present invention is a bone conduction speaker.
Figure 4:
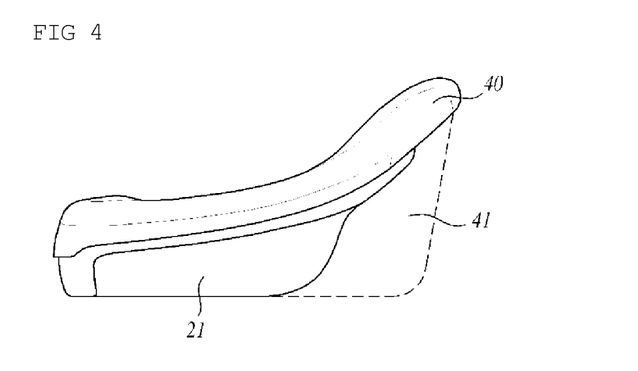
FIG. 4 is a side view illustrating a functional pillow according to an embodiment of the present invention.
Figure 5A:
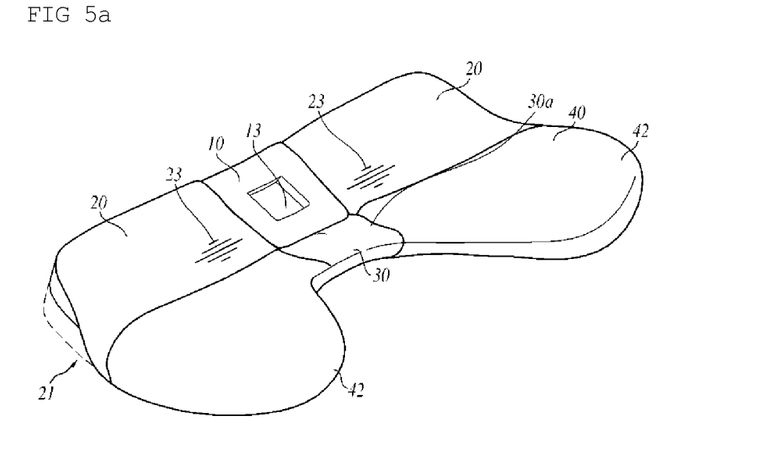
FIG. 5a is a perspective view illustrating a functional pillow according to another embodiment of the present invention.
Figure 5B:
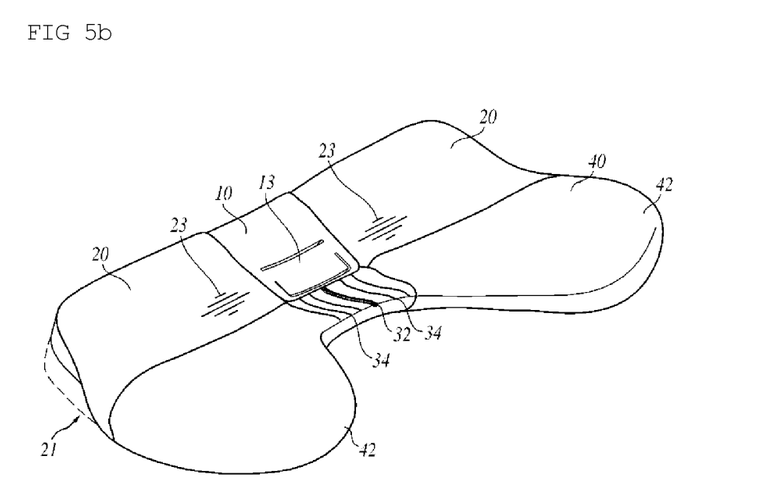
FIG. 5b is a perspective view illustrating a functional pillow according to another embodiment of the present invention.
Figure 6:
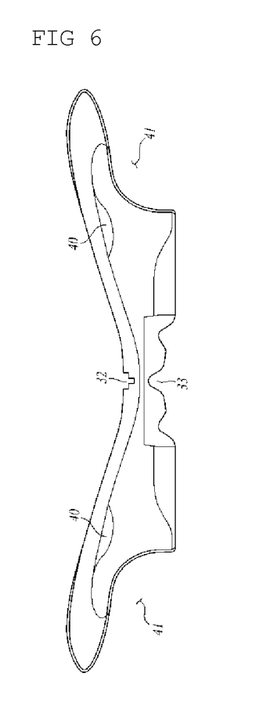
FIG. 6 is a front view illustrating a functional pillow according to still another embodiment of the present invention.
Figure 7:
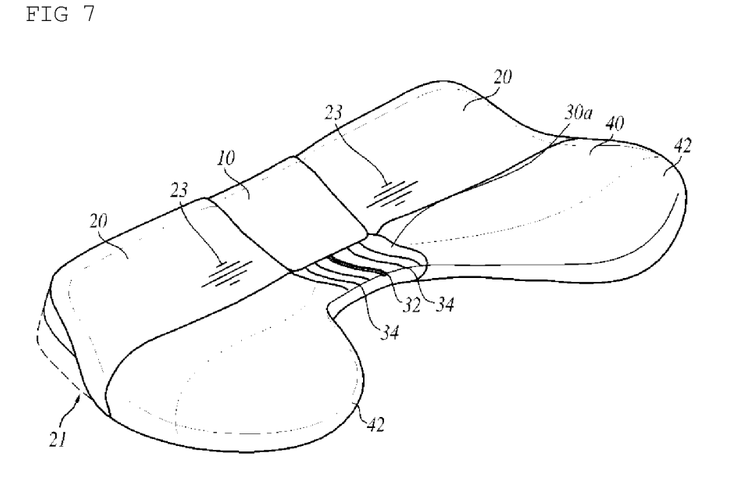
FIG. 7 is a perspective view of FIG. 6.
Figure 8:
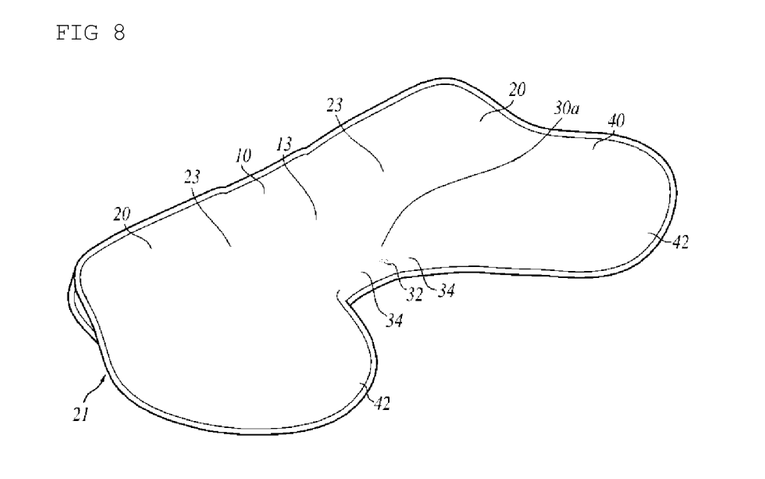
FIG. 8 is a perspective view illustrating a state in which a functional pillow according to an embodiment of the present invention is inserted into a pillow cover.
Figure 9:
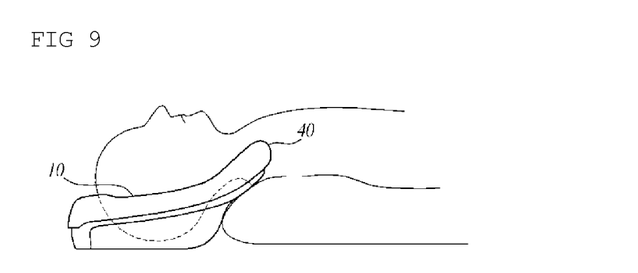
FIG. 9 is a view illustrating a use state of a functional pillow according to an embodiment of the present invention.
Figure 10:
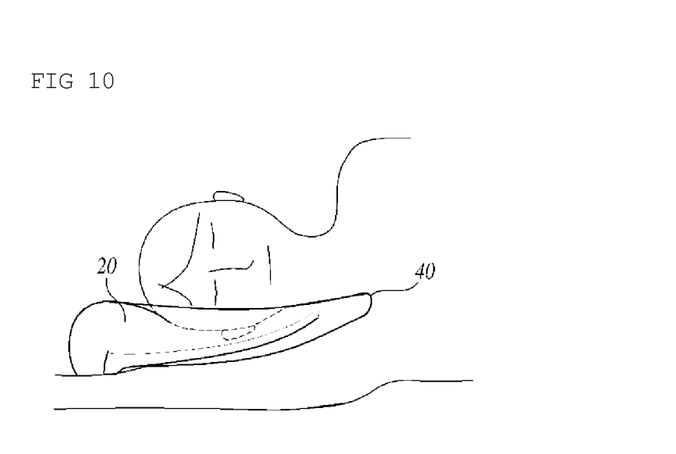
FIG. 10 is a view illustrating a use state of a functional pillow according to an embodiment of the present invention.
Figure 11:
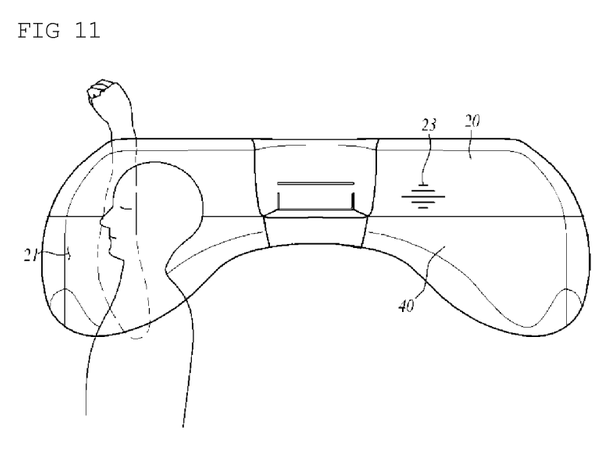
FIG. 11 is a view illustrating a use state of a functional pillow according to an embodiment of the present invention.

FIG. 1 is a perspective view illustrating a functional pillow according to an embodiment of the present invention, FIG. 2 is a plan view illustrating a functional pillow according to an embodiment of the present invention, FIGS. 3a to 3c are rear views illustrating a functional pillow according to an embodiment of the present invention, FIG. 3b is an exemplary view illustrating a process of inserting a first height adjustment pad and a sound source generator according to an embodiment of the present invention, FIG. 3c is an exemplary view illustrating a case in which a sound source generator according to an embodiment of the present invention is a bone conduction speaker, FIGS. 5a and 5b are perspective views illustrating a functional pillow according to another embodiment of the present invention, FIG. 6 is a front view illustrating a functional pillow according to still another embodiment of the present invention, FIG. 7 is a perspective view of FIG. 6, FIG. 8 is a perspective view illustrating a state in which a functional pillow according to an embodiment of the present invention is inserted into a pillow cover, and FIGS. 9 to 11 are views illustrating use states of a functional pillow according to an embodiment of the present invention.

As illustrated in FIGS. 1 to 8, a functional pillow according to embodiments of the present invention includes a back head placement part 10, a pair of core parts 20, a cervical vertebra support part 30, and a pair of wing parts 40.

The back head placement part 10 is formed of a material with predetermined shape and thickness, and configured to allow the back of a user's head to be placed on an upper surface thereof. The back head placement part 10 may be formed in, for example, a rectangular shape, and, if necessary, may be formed in a circular shape, an elliptical shapes, or a combined shape of circular and rectangular shapes.

The core part 20 is formed at both sides of the back head placement part 10, and the cervical vertebra support part 30 is formed on an upper side of the back head placement part 10. Here, the back head placement part 10 may be preferably formed at a height about half of a total height of the core part 20.

Also, at least one first pressure distribution part 13 may be formed in the back head placement part 10 so as to distribute the load pressure from the back of the user's head. For example, the first pressure distribution part 13 may include one ⊏-shaped line formed to penetrate a portion adjacent to the cervical vertebra support part, and at least one straight line the back head placement part 10 formed to be spaced apart from the ⊏-shaped line and formed to penetrate. These lines are designed to distribute the load pressure of the back head and thus allow the load pressure of the back head to be uniformly distributed regardless of shapes of users' back heads. Thus, sleep comfort may be maximized.

Besides these shapes, the first pressure distribution part 13 may be formed in the form of a groove having a shape of a polygon, a circle, an ellipse, or a combination thereof. Alternatively, the first pressure distribution part 13 may be formed to penetrate in a shape of a polygon, a circle, an ellipse, or a combination thereof. FIG. 5a exemplarily illustrates the first pressure distribution part 13 is formed in a rectangular groove shape.

In the case of a typical pillow, sleep is affected by a pressure felt due to the concentration of a load at a most protruded feature portion when the back of the user's head touches the surface of the pillow. Conversely, according to a functional pillow according to an embodiment of the present invention, for example, since the surface of the back head placement part 10 coupled to the core part 20 at a half height of the core part uniformly distributes the load pressure of the back of the user's head to the entire back head placement part 10, sleep comfort may be maximized.

Also, a plurality of holes (not shown) may be formed in a predetermined size on a surface of the back head placement part 10. The hole part (not shown) functions to uniformly distribute the back head load pressure of a user to the entire back head placement part 10, and increases air permeability to allow the user to feel cool. Thus, sleep comfort may be maximized.

A functional pillow according to an embodiment of the present invention may further include a first height adjustment pad PI which may be inserted into a lower space of the back head placement part. (see FIG. 3b)

The first height adjustment pad PI may be formed in a shape corresponding to the shape of the back of the user's head. That is, to meet the needs of unspecified individual users, various shapes of users' back heads are modeled, and shape patterns of upper surfaces of the first height adjustment pads PI are accordingly treated to provide the plurality of first height adjustment pad PI as a set. Thus, one product may even be allowed to be used regardless of shapes of users' back heads. Here, the material of the first height adjustment pad PI may have hardness greater than that of the back head placement part. By increasing the hardness of the first height adjustment pad PI, the back of the user's head corresponding to the configuration of the first height adjustment pad may feel more stability.

Like the surface of the back head placement part 10, a plurality of holes (not shown) may be formed in predetermined sizes. The hole part (not shown) functions to uniformly distribute the back head load pressure of a user to the first height adjustment part and the entire back head placement part 10, and increases air permeability to allow the user to feel cool. Thus, sleep comfort may be maximized. [70]

The pair of core parts 20 are formed to extend in directions of both sides of the back head placement part. Here, the core parts 20 preferably extend to be inclined at a predetermined angle from the back head placement part. That is, the back head placement part and the pair of core parts are preferably coupled to each other to incline at a predetermined angle such that when a user lies on the back, the back of the user's head is allowed to be placed on the back head placement part, and when a user lies on the side, user's face is supported by any one of the pair of core parts.

The pair of core parts 20 and the cervical vertebra 30 may be formed in a multilayer structure including two or more materials with different hardness, and may be formed such that the hardness of a lower layer is greater than that of an upper layer. As described above, a front surface of the pillow may be made softer and a rear surface of the pillow may be made relatively harder by allowing the hardness of the lower layer to be greater and the hardness of the upper layer to be softer.

The core part 20 supports the load of the head when a user sleeps on the side. For this, a concave portion with a predetermined size may be formed on an upper surface of the core part 20 to correspond to the shape of the human face (the shape of the cheek).

Also, second pressure distribution parts 23 and 24 may be formed in the core parts 20 such that load pressure of the side head portion (particularly, a pressure felt adjacent to the ear) occurring when a user sleeps on the side may be solved. The second pressure distribution parts 23 and 24 may be formed on an upper surface or a lower surface, and may be also simultaneously formed on the upper and lower surfaces of the core part 20.

At least one pressure distribution groove 23 may be formed on the upper surface of the core part 20. The pressure distribution groove 23, which is formed by cutting the upper surface of the core part 20 at a predetermined depth through a cutting means such as die, cutter, may be formed at a predetermined depth or to penetrate from the upper surface of the core part 20. The pressure distribution groove 23 is to distribute load pressure of a user face (particularly, a pressure felt adjacent to the ear) occurring because the hardness of the lower portion of the core part 20 is greater than that of the upper portion when a user sleeps on the side (see FIG. 11). At least three of more pressure distribution holes 23 are preferably formed so as to be all applied to various sizes and shapes of users. Here, when the pressure distribution grooves 23 are formed in the same size, there may be a bad effect to the durability of the pillow. Therefore, the middle of the grooves is formed in the largest size and the upper and lower grooves are formed in gradually reduced size in upward and downward directions, respectively.

The pressure distribution spaces 24 (see FIG. 3*a*) may be formed in a center of the lower surface of the core part 20. The pressure distribution spaces 24, which is formed in a predetermined size on a lower surface of the core part 20, is preferably formed at a portion adjacent to the cervical vertebra support part 30 or a wing part 40.

Also, referring to FIG. 3*b*, a sound source generator M capable of providing music for inducing sleep to a user while sleeping may be accommodated in the pressure distribution space 24. The sound source generator M may be a music player such as a radio, an MP3, a cassette. Here, a through hole (not shown) may be formed in the core part 20 such that a user may effectively listen to the sound generated from the sound source generator M. Of course, when the pressure distribution grooves 23 are formed on the upper surface of the core part 20 and the pressure distribution space 24 are formed on the lower surface of the core part 20, the pressure distribution grooves 23 may simultaneously perform the function of the through hole.

Alternatively, as illustrated in FIG. 3*c*, the sound source generator M may be a speaker, particularly a bone conduction speaker. That is, the bone conduction speaker is accommodated in the pressure distribution space 24, and a terminal connected to the bone conduction speaker is connected to a mobile terminal S such as a smart phone, so that a sound source played at the mobile terminal S may be propagated through the bone conduction speaker accommodated in the pressure distribution space 24. Here, a sound source application for sleeping may be installed to the mobile terminal, and the sound source application for sleeping may include various sound source play modes. For example, a deep sleep mode, a stabilization mode, a hypnosis node, a brainwave tuner mode, etc. may be provided.

In lower portions of both ends of the core parts 20, spaces 21 into which arms of a user may be inserted when the user lift the arms at a predetermined angle while sleeping on the side are formed. Accordingly, when a user sleeps on the side, the pillow is prevented from being deviated from a suitable sleeping position by an arm motion.

Ends 22 of the core parts upwardly protrude to prevent the face of a user from deviating therefrom. Also, a pad insertion part (not shown) into which a second height adjustment pad (not shown) capable of adjusting the height of the pair of core parts may be formed at a lower end of the pair of core parts 20. Here, the second height adjustment pad may be preferably formed of a material with hardness greater than that of the pair of core parts.

The cervical vertebra support part 30 is formed to be coupled to the back head placement part 10 and the pair of core parts 20, and protrudes from the back head placement part to be coupled with inclination. The cervical vertebra support part 30 is preferably formed to have a central portion with a height lower than those of both side portions thereof. Accordingly, the cervical vertebra of a user may be stably positioned at the cervical vertebra support part 30.

Also, at least one groove with predetermined shapes may be formed at a predetermined position of the cervical vertebra support part 30 on which the cervical vertebra of a user is placed such that the pressure due to the cervical vertebra may be distributed (see FIG. 5*b*). For example, the groove may be formed in a T-shaped form 32. Also, for example, the grooves may be a vertically formed straight shape 34. Also, for example, the grooves may be formed in a combination of the T-shaped form 32 and the straight shape 34.

Also, the cervical vertebra support part 30 may be formed as a multilayer structure formed of one or more materials with different hardness. Preferably, the cervical vertebra support part 30 may be formed such that the hardness of a lower layer 30B of the cervical vertebra support part is greater than that of an upper layer 30A.

Since the hardness of the lower layer 30B of the cervical vertebra support part is greater than that of the upper layer 30A, a user may feel both softness and stability. That is, since the lower layer 30B is relatively hard, the sense of stability may be provided, and since the upper layer 30A is not relatively hard, the sense of softness may be provided. It is sufficient only if the hardness of the lower layer 30B is a degree capable of giving acupressure to and retracting the neck before sleeping. That is, a user may turn over and use the pillow before sleeping. Here, since the lower layer 30B is relatively hard, user's neck may be given acupressure and retracted.

Also, at least a part of the cervical vertebra support part may include a cervical vertebra acupressure part 31 formed with hardness greater than those of the upper and lower layers.

The cervical vertebra acupressure part 31 may be formed such that a material with hardness greater than those of the upper and lower layers is applied for surface treatment, or the material with hardness greater than those of the upper and lower layers is inserted into or attached to the cervical vertebra acupressure part 31. For example, the cervical vertebra acupressure part 31 may be formed such that the hardness thereof is relatively greater than other portion of the functional pillow by spraying polyurea thereto. Alternatively, plastic, metal, wood, etc. having hardness greater than those of the material of the pillow may be attached to the lower layer 30B of the cervical vertebra by using an attaching means. Alternatively, the cervical vertebra acupressure part 31 may be formed by providing a space into which plastic, metal, wood, etc. may be inserted in the lower layer 30B of the cervical vertebra support part and inserting the plastic, metal, wood, etc.

Unlike the cervical vertebra acupressure part 31 which is a type attached to or inserted into the pillow, a detachable type cervical vertebra acupressure part (not shown) which may also be attached to or detached from the pillow. For this, any one side of a Velcro tape (referred to as a hook and loop fastener), which includes hooks at one side and loops at the other side, is formed at a predetermined position of the lower layer 30B of the cervical vertebra support part, and the other side of the Velcro tape is formed at the cervical vertebra acupressure part 31. Then, the cervical vertebra acupressure part may be used by being attached to the lower layer 30B of the cervical vertebra support part, and detached and stored after use. In this case, a pillow insertion zipper for inserting the pillow and a cervical vertebra acupressure part insertion zipper for inserting the cervical vertebra acupressure part are formed in the cover of the pillow, and thus attachment/detachment of the cervical vertebra acupressure part may be easily performed.

Like this, by forming the cervical vertebra acupressure part 31 as a fixed type or a detachable type, when a user turns over the functional pillow before sleeping and allows the cervical vertebra to be in contact with the cervical vertebra acupressure part, the user may achieve effects of acupressure and retraction of the cervical vertebra (neck retraction) through the hard portion of the cervical vertebra acupressure part 31.

Also, at least one groove 32 and 33 allowing the pressure due to the cervical vertebra of a user to be distributed may be formed at upper and lower surfaces of the cervical vertebra support part and the back head placement part (see FIGS. 6 and 7). The grooves 32 and 33 allows the pillow to be concentrated toward the cervical vertebra of the user, and a comfortable feeling may be transmitted, and allows the hard cervical vertebra acupressure part 31 to be concentrated toward the cervical vertebra when performing cervical vertebra acupressure before sleeping, so that effects of acupressure and retraction may be improved.

A pair of mastoid zones 15 which distribute load pressure due to the neck and back head of a user may be formed at both ends of the lower layer of the cervical vertebra support part 30. In addition, a penetration zone 16 may be formed between the mastoid zones 15 in a direction substantially parallel to the mastoid zones 15. These mastoid zones 15 and the penetration zone 16 uniformly distribute loads of the neck and head of a user while sleeping, thereby maximizing sleep comfort. Here, the mastoid zones 15 are preferably formed in a size from about 70% to about 100% of the width W of the lower layer in comparison with the width of the lower layer 30B of the cervical vertebra acupressure. When the sizes of the mastoid zones 15 are less than about 70% in comparison with the width W, the effect of distributing load pressure may be insufficient and pressure may be felt and thus may affect the sleep of a user.

When the mastoid zones 15 and the penetration zone 16 do not exist at both ends of the lower layer of the cervical vertebra support part 30, both sides of the back head part of a user are pressed by the cervical vertebra support part 30 when a user uses the pillow. To prevent this, the mastoid zones 15 and/or the penetration zone 16 are formed at both ends of the lower layer of the cervical vertebra support part 30 to reduce the sense of being pressed, and the mastoid zones 15 are formed at both ends of the lower layer of the cervical vertebra support part 30 to achieve effects of maximizing the comfort when placing the head portion and more lifting of the wing parts of both sides while the mastoid zones 15 are widened by the load of user's head. Also, when the pillow is turned over and used, the mastoid zones 15 may perform a function of carefully surrounding the head while being contracted.

The pair of core parts 20 and the cervical vertebra support part 30 may be formed in a multilayer structure including two or more materials with different hardness, and may be formed such that the hardness of a lower layer is greater than that of an upper layer. As described above, a front surface of a pillow may be made softer and a rear surface of the pillow may be made relatively harder by allowing the hardness of the lower layer to be greater and the hardness of the upper layer to be softer.

As described above, the hardness of a front surface of a pillow is made softer and a rear surface of the pillow is made harder, and thus a user may use the rear surface of the pillow for a simple acupressure and a retraction before sleeping.

Also, filter foam with greater hardness may be integrally formed on the entire portion or one portion of the rear surface of the pillow. When manufactured like this, the rear surface of the pillow may be more firmly formed and the total height of the pillow may be increased by the characteristic of the filter foam. For example, a pillow manufactured like this by forming the filter foam has a merit of being specialized for men.

The pair of wing parts 40 extend to be upwardly inclined at one side of the pair of core parts and is formed in a shape supporting user's face by being inserted between the face and user's shoulder when the user lies on the side. Here, both corner sides 42, which are not coupled to the cervical vertebra support part, of the pair of wing parts 40 is formed to extend longer in an upwardly inclined direction than the portion coupled to the cervical vertebra support part 30, and an end of the pair of wing parts is preferably formed to protrude than the other end. Since the ends of the wing parts are formed to protrude, when a user lies on the side, user's shoulder is positioned at a space 41 under the wing parts while user's face is placed on the upper surface of the core parts 20, and the wing parts 40 is tightly disposed between user's face and shoulder and may support user/s face.

Since the wing part 40 is thus formed to extend with an inclination, a space into which user's shoulder may be inserted is formed thereunder, and user/s shoulder may be inserted into the space when the user sleeps on the back.

Also, the wing parts 40 are naturally positioned between the neck and shoulder when the user sleeps on the back and then sleeps on the side. Accordingly, user's neck may be prevented from being downwardly folded or bent by a load. As a result, the disease of the neck and shoulder caused by the overstress of the shoulder joint or the torsion of the cervical vertebra which are frequently experienced by the people sleeping on the side.

FIG. 8 illustrates a state in which a functional pillow according to an embodiment of the present invention is inserted in a pillow cover A.

Next, a method of using the functional pillow according to an embodiment of the present invention will be described with reference to FIGS. 9 to 11.

FIG. 9 is a view illustrating a functional pillow used when a user sleeps on the back.

As illustrated in FIG. 9, when a user sleeps on the back, the back of the user's head is placed on the back head placement part 10, the user's neck is placed on the cervical vertebra support part, and user's shoulder is inserted into the space formed under the wing part 40. Here, the back of the user's head may be placed on a portion of the first pressure distribution part, and ⊏-shaped line of the first pressure distribution part distributes the pressure load of the back head while moving downward by the load pressure of the back head. As a result, sleep comfort is allowed to be maximized for a user.

FIGS. 10 and 11 are views illustrating use states of a functional pillow when a user sleeps on the side. FIG. 10 is a side view, and FIG. 11 is a plan view.

As illustrated in FIG. 10, when a user is changed to sleep on the side while sleeping on the back regardless of whether by intention or not, user's face is moved from the back head placement part to the core part 20, and accordingly, the wing part 40 is naturally positioned between user's neck and shoulder. Accordingly, the user's neck may be prevented from being downwardly folded or bent by a load. As a result, the disease of the neck and shoulder caused by the overstress of the shoulder joint or the torsion of the cervical vertebra which are frequently experienced by the people sleeping on the side.

According to the above-described functional pillow according to an embodiment of the present invention, when sleeping on the back, user's neck and head are comfortably supported, and even when sleeping on the side, the pressure of user's shoulder or the deflection of user's neck are prevented, and thus may automatically maintain a balance of the cervical vertebra.

Also, by preventing the pressure of user's shoulder or the deflection of user's neck even when sleeping on the side, there is a merit in that the disease of the neck and shoulder caused by the overstress of the shoulder joint or the torsion of the cervical vertebra which are frequently experienced by the people sleeping on the side.

Also, when a user turns over the functional pillow before sleeping and allows the cervical vertebra to be in contact with the cervical vertebra acupressure part, the user may achieve effects of acupressure and retraction of the cervical vertebra (neck retraction) through the hard portion of the cervical vertebra acupressure part 31.

Although preferred embodiments are illustrated and described above, the specification is not limited to a specific embodiment mentioned above. Various modifications are possible by those skilled in the art without departing from the spirit and scope of the claims. Also, such modifications should not be understood separately from the spirit and scope of the inventive concept.

DESCRIPTION OF REFERENCE NUMERALS

10: back head placement part
13: first pressure distribution part
15: mastoid zone
16: penetration zone
20: core part
21, 41: space
23, 24: second pressure distribution part
30: cervical vertebra support part
40: wing part

What is claimed is:

1. A functional pillow comprising:
   a back head placement part formed of a material with a predetermined shape and thickness and allowing the back of a user's head to be placed thereon when the user lies on a back of the user, wherein the back head placement part further comprises:
   an upper surface on which the back of the user's head is placed;
   a lower surface that defines a height adjustment space; and
   at least one first pressure distribution part on the upper surface thereof to distribute load pressure due to the back of the user's head, wherein the at least one first pressure distribution part comprises a ⊏-shaped line and at least one straight line penetrating the upper surface of the back head placement part;
   a pair of core parts coupled to the back head placement part, defining an arm space, into which a user's arm is allowed to be inserted, under both ends thereof, and configured to support a user's face on an upper surface thereof when the user lies on a user's side while the back of the user's head is placed on the back head placement part, wherein the at least one straight line is a horizontal line extending between the pair of core parts;
   a cervical vertebra support part coupled to the back head placement part, and protruding with an inclination from the back head placement part to support cervical vertebra, wherein the pair of core parts and the cervical vertebra support part are formed in a multilayer structure formed of two or more materials with different hardness, and the hardness of a lower layer is greater than that of an upper layer, wherein a pair of mastoid zones distributing load pressure due to a user's neck and the back of the user's head are formed at both lower ends of the cervical vertebra support part; and
   a pair of wing parts formed to be directly coupled to the pair of core parts and the cervical vertebra support part, formed to be upwardly bent with an inclination, and defining a shoulder space, into which a user's shoulder is allowed to be inserted, thereunder, wherein the wing parts are formed in a shape supporting the user's face by being inserted between the user's face and the user's shoulder when the user lies on the user's side.

2. The functional pillow as set forth in claim 1, wherein the back head placement part and the pair of core parts are coupled to each other to incline at a predetermined angle such that when the user lies on the user's back, the back of the user's head is allowed to be placed on the back head placement part, and when the user lieson the user's side, the user's face is supported by any one of the pair of core parts.

3. The functional pillow as set forth in claim 1, wherein the ends of the pair of core parts upwardly protrude to prevent the user's face from being deviated.

4. The functional pillow as set forth in claim 1, wherein the core parts further comprises at least one second pressure distribution part allowing load pressure due to a side of the user's head to be distributed.

5. The functional pillow as set forth in claim 4, wherein the at least one second pressure distribution part is formed on at least one surface of upper and lower surfaces of the core parts.

6. The functional pillow as set forth in claim 4, wherein the second pressure distribution part is cut to a predetermined depth from an upper surface of the core parts.

7. The functional pillow as set forth in claim 4, wherein the at least one second pressure distribution part comprises at least one pressure distribution groove formed on the upper surfaces of the core parts, and pressure distribution spaces defined on the lower surfaces of the core parts.

8. The functional pillow as set forth in claim 7, wherein the at least one pressure distribution spaces are formed at portions adjacent to the cervical vertebra support part or the wing part.

9. The functional pillow as set forth in claim 7, further comprising a sound source generator accommodated in the pressure distribution space.

10. The functional pillow as set forth in claim 1, further comprising a first height adjustment pad allowed to be inserted into the height adjustment space.

11. The functional pillow as set forth in claim 10, wherein the first height adjustment pad comprises a hole portion capable of distributing load pressure due to the back of the user's head and increasing air permeability.

12. The functional pillow as set forth in claim 1, wherein at lower ends of the pair of core parts, pad insertion parts into which second height adjustment pads allowing heights of the pair of core parts to be adjusted are formed.

13. The functional pillow as set forth in claim 12, wherein the second height adjustment pads are formed of materials with hardness greater than those of the upper and lower layers of the pair of core parts.

14. The functional pillow as set forth in claim 1, wherein the cervical vertebra support part comprises a cervical vertebra acupressure part formed to have hardness greater than those of the upper and lower layers of the cervical vertebra support part.

15. The functional pillow as set forth in claim 14, wherein the cervical vertebra acupressure part comprises a surface treated by a material having hardness greater than those of the upper and lower layers of the cervical vertebra support part, or comprises a portion formed such that a material having hardness greater than those of the upper and lower layers of the cervical vertebra support part is inserted into or attached to the portion.

16. The functional pillow as set forth in claim 14, wherein the cervical vertebra acupressure part is formed to be attached/detached to a lower layer of the cervical vertebra support part.

17. The functional pillow as set forth in claim 1, wherein the pair of wing parts are formed in shapes supporting user's jaw and neck by being inserted between a user's neck and shoulders when the user lieson the user's side.

* * * * *

UNITED STATES PATENT AND TRADEMARK OFFICE
CERTIFICATE OF CORRECTION

PATENT NO. : 10,080,450 B2  
APPLICATION NO. : 14/951249  
DATED : September 25, 2018  
INVENTOR(S) : Joon Shik Shin et al.

Page 1 of 1

It is certified that error appears in the above-identified patent and that said Letters Patent is hereby corrected as shown below:

In the Claims

In Claim 2, Column 12, Line 9, delete "lieson" and insert --lies on--

In Claim 17, Column 13, Line 8, delete "lieson" and insert --lies on--

Signed and Sealed this  
Twentieth Day of November, 2018

Andrei Iancu  
*Director of the United States Patent and Trademark Office*